US012758414B2

(12) United States Patent
Michael

(10) Patent No.: US 12,758,414 B2
(45) Date of Patent: Oct. 13, 2026

(54) LUMBAR SPINE ORTHOSIS WITH MECHANICAL CINCHING DEVICE

(71) Applicant: James Edward Michael, Danville, CA (US)

(72) Inventor: James Edward Michael, Danville, CA (US)

( * ) Notice: Subject to any disclaimer, the term of this patent is extended or adjusted under 35 U.S.C. 154(b) by 0 days.

(21) Appl. No.: 18/933,208

(22) Filed: Oct. 31, 2024

(65) Prior Publication Data

US 2025/0134691 A1 May 1, 2025

Related U.S. Application Data

(60) Provisional application No. 63/594,632, filed on Oct. 31, 2023.

(51) Int. Cl.
*A61F 5/02* (2006.01)

(52) U.S. Cl.
CPC .................................... *A61F 5/028* (2013.01)

(58) Field of Classification Search
CPC .. A61F 5/02; A61F 5/022; A61F 5/024; A61F 5/026; A61F 5/028; A61F 5/03; A61F 5/0123; A61F 5/0118; A61F 5/30; A61F 5/01; A61F 5/0106; A61F 5/0111; A61F 2005/0132; A61F 2005/0176; A61F 13/102; A61F 13/108; B25B 15/04; A44B 11/00–28; A41D 13/065; A41D 13/0568; A61B 17/132; A61B 17/1325
USPC ............................................................ 602/19
See application file for complete search history.

(56) References Cited

U.S. PATENT DOCUMENTS

| | | | | |
|---|---|---|---|---|
| 3,095,875 | A * | 7/1963 | Davidson | A61F 5/024 602/19 |
| 3,274,996 | A * | 9/1966 | Jewett | A61F 5/024 602/19 |
| 3,926,182 | A | 12/1975 | Stabholz | |
| 5,351,340 | A * | 10/1994 | Aldridge | A61F 5/028 2/81 |
| 9,414,955 | B2 | 8/2016 | Safko et al. | |
| 10,264,835 | B2 | 4/2019 | Ingimundarson et al. | |
| 10,828,186 | B2 | 11/2020 | Ingimundarson et al. | |
| 10,952,509 | B2 * | 3/2021 | Simpson | A44B 11/125 |
| 11,213,419 | B2 | 1/2022 | DiAngelo et al. | |
| 11,484,428 | B2 | 11/2022 | Ingimundarson et al. | |
| 11,571,323 | B2 | 2/2023 | Ingimundarson et al. | |
| 2001/0008955 | A1 | 7/2001 | Garth | |
| 2003/0213343 | A1 * | 11/2003 | Schuster | B25G 1/007 81/73 |

(Continued)

*Primary Examiner* — Daniel A Miller
(74) *Attorney, Agent, or Firm* — Dunlap Bennett & Ludwig PLLC

(57) ABSTRACT

A lumbar spine brace provides posterior support connected to an approximate midpoint of a flap, wherein the flap extends between a first end and a second end. The flap provides a longitudinal channel through which a cinching band is disposed, wherein a male end of the cinching strap protrudes from on opening along the first end. A captured screw directly connects to the second end of the flap, wherein the captured screw provides a tool interface communicating with an external environment, wherein the cinching band is dimensioned and shaped to operatively associate with the captured screw that is rotatable via the tool interface whereby a circumferential compressive force is imparted on the flap.

10 Claims, 6 Drawing Sheets

(56) References Cited

U.S. PATENT DOCUMENTS

| | | | | |
|---|---|---|---|---|
| 2004/0231468 | A1* | 11/2004 | Odachowski ....... B25B 23/0042 81/58.1 |
| 2009/0163841 | A1* | 6/2009 | Garth ...................... A61F 5/028 602/19 |
| 2009/0192425 | A1 | 7/2009 | Garth et al. |
| 2010/0199473 | A1 | 8/2010 | Long et al. |
| 2013/0087141 | A1 | 4/2013 | Williams |
| 2013/0158457 | A1 | 6/2013 | Garth et al. |
| 2013/0237891 | A1 | 9/2013 | Fryman et al. |
| 2013/0289461 | A1 | 10/2013 | Cropper et al. |
| 2014/0364786 | A1 | 12/2014 | Haider et al. |
| 2015/0112239 | A1 | 4/2015 | Hinshon et al. |
| 2016/0135547 | A1* | 5/2016 | Kuffrey .................... B25H 3/00 482/93 |
| 2016/0193982 | A1 | 7/2016 | Wu |
| 2016/0296361 | A1 | 10/2016 | Leake et al. |
| 2016/0310311 | A1* | 10/2016 | Haje ......................... A61F 5/02 |
| 2018/0280182 | A1* | 10/2018 | Turrini .................... A61F 5/028 |
| 2019/0231576 | A1 | 8/2019 | Lawrence |
| 2020/0179152 | A1 | 6/2020 | Yampolsky et al. |

* cited by examiner

LUMBAR SPINE ORTHOSIS WITH MECHANICAL CINCHING DEVICE

CROSS-REFERENCE TO RELATED APPLICATION

This application claims the benefit of priority of U.S. provisional application No. 63/594,632, filed 31 Oct. 2023, the contents of which are herein incorporated by reference.

BACKGROUND OF THE INVENTION

The present invention relates to lumbar spine braces and, more particularly, a lumbar spine orthosis with a mechanical cinching device.

Adequate and considerable circumferential lumbar compression from a lumbar spine brace is required for it to function as, in essence, an external strut for treating lumbar spine pathologies (i.e., spondyloarthropathies, instability, generalized centralized low back pain, low back pain with radiculopathies and spondylolisthesis-slippage of vertebrae). Lumbar spine braces today require the patient or a patient's aide to manually tighten the brace by pulling overlapping Velcro™ flaps tightly around the patient's waist or even utilizing "pull cords", which is a secondary tightening mechanism to try and acquire appropriate and adequate lumbar spine external compression support. This is extremely difficult and unattainable for most people who require lumbar spine support either because they are geriatric with senile asthenia or have other upper extremity impediments that limit their manual strength and dexterity.

In other words, patients that require lumbar spine braces generally do not have the strength due to neuromusculoskeletal pathology to properly apply the brace. And so, these patients require a partner or aide to adequately tighten the brace. And even with another person it is difficult to apply the lumbar spine brace as the patient will require the ability to counteract the anterior vectored force of pulling and overlapping the hook and loop flaps, all while balancing during this tightening process. Unfortunately, this will likely be inadequate as there are too many dynamic factors at play: the patient's strength to counteract the anterior force, their balance, whether or not the patient has an aide available and the aide's strength assisting with the brace.

In sum, current solutions require dexterity, strength and stability of the patient when applying a lumbar spine brace to be effective, yet the compression required is beyond the patient's means due to upper extremity pathologies (i.e., arthritis, neurodegenerative conditions, generalized senile asthenia, etc.).

As can be seen, there is a definitive need for a lumbar spine brace with a mechanical cinching device for patients unable to manually tighten the brace, thereby allowing the patient to apply the brace and utilize a systemic tool to cinch the brace to the desired and appropriate amount of external compression without requiring excessive strength or dexterity.

SUMMARY OF THE INVENTION

The present invention allows the patient to apply the lumbar spine brace as if they were donning an abdominal binder/corset and mechanically compressing and/or cinching utilizing a hex nut driver to tighten the brace through a cinching mechanism integrated into the brace. The present invention is adapted to obviate the need for significant upper body strength to pull the primary flaps sufficiently to ensure the brace is functional and effective in maintaining an adequate and appropriate external strut for instability in the spine.

The lumbar spine brace/support of the present invention has an intrinsic cinching mechanism within a primary flap for the brace itself. The cinching mechanism may be a semirigid curvilinear fiberglass band that is exposed on either end through the opposing ends of the primary flap. The band of the cinching mechanism may have a male end that interacts with a female end. The primary flap may have complementary hook and loop fasteners to set and maintain an easy-to-achieve initial engagement between the brace and the patient prior to engaging the cinching mechanism. The cinching mechanism may have a hex bolt accessible externally to the primary flap that is tightened with an ergonomic handheld hex driver, thereby making the task of properly compressing the brace around the patient easy for patients with an upper extremity neuromusculoskeletal pathology or generalized weakness and lack of dexterity to manipulate. Patients with strokes that have spasticity (Ashworth less than or equal to 2) and/or spinal cord injuries (caudal to cervical vertebrae 6) will be able to manipulate the hex driver.

The present invention allows patients to tighten the brace to an acceptable, adequate, and appropriate amount of compression without requiring manual strength of pulling, overlapping, and maintaining relative positions of primary flaps that then need to be secured.

Said primary flap extends between a first end and a second end; the flap may provide a longitudinal channel through which a cinching band is disposed, wherein a male end of the cinching strap protrudes from on opening (of the primary flap) along the first end, while a captured screw is directly connected to the second end of the flap. The captured screw provides a tool interface communicating with an external environment, wherein the cinching band is dimensioned and shaped to operatively associate with the captured screw that is rotatable via the tool interface whereby a circumferential compressive force is imparted on the primary flap via the circumferential compression of the cinching band.

In another aspect of the present invention, the lumbar spine brace further includes wherein the captured screw is disposed in a housing that is clipped directly to the second end of the primary flap, wherein the captured screw directly integrated with the cinching band, at or adjacent its female end, wherein the first and second ends of the primary flap provide hook and loop fasteners, respectively for establishing an initial secured condition, from which the circumferential compressive force further cinches formed by way of the initial secured condition, wherein the cinching band provides a screw thread pattern for operatively associating with the captured screw, wherein the tool interface comprises a hex bolt interface; further providing a systemic tool having a hex driver dimensioned and shaped to operatively associate with the hex bolt interface, wherein the hex driver is electrically powered, or wherein the systemic tool provides a working handle directly connected to an articulating ratcheting joint, which in turn is directly connected to a stabilizing handle directly connected to a magnetic hex driver. The handle is ergonomically fashioned so that patients who lost dexterity and intrinsic appositive strength in their hands yet maintained shoulder and/or elbow strength may independently mechanistically circumferentially tighten the brace adequately.

In another aspect of the present invention, a lumbar spine brace includes the following: a posterior lordotic arch support that is connected to an approximate posterior midpoint of the primary flap. The posterior lordotic arch support is operatively associated with an adjustable vertical channel that is also associated with the primary flap so as to enable appropriate positioning (in the cephalad-caudad orientation i.e. coronal plane) at the lumbar vertebrae 4 and lumbar vertebrae 5 (L4-L5) level.

These and other features, aspects and advantages of the present invention will become better understood with reference to the following drawings, description and claims.

DETAILED DESCRIPTION OF THE INVENTION

Figure 1:
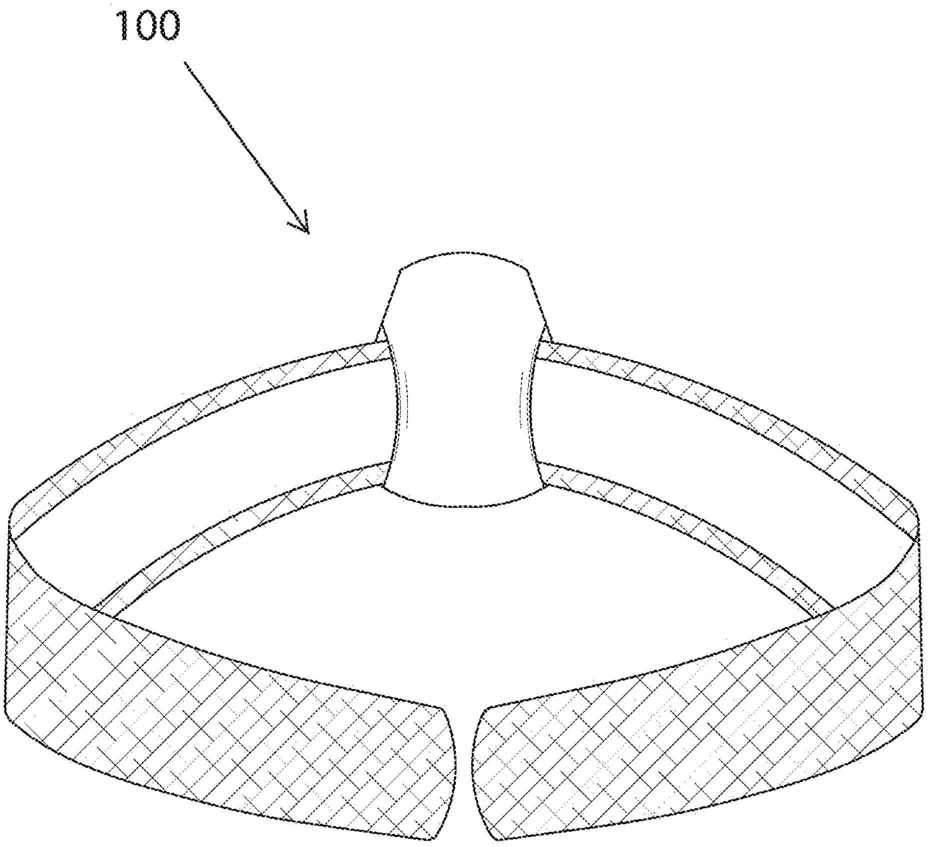
FIG. 1 is a perspective view of an exemplary embodiment of the present invention.
Figure 2:
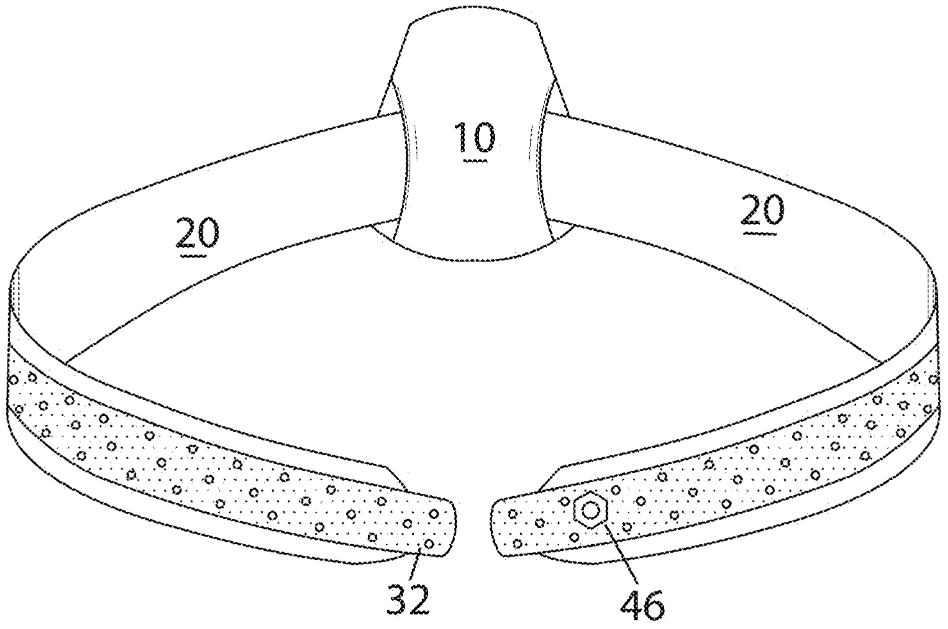
FIG. 2 is a perspective view of an exemplary embodiment of the present invention.
Figure 3:
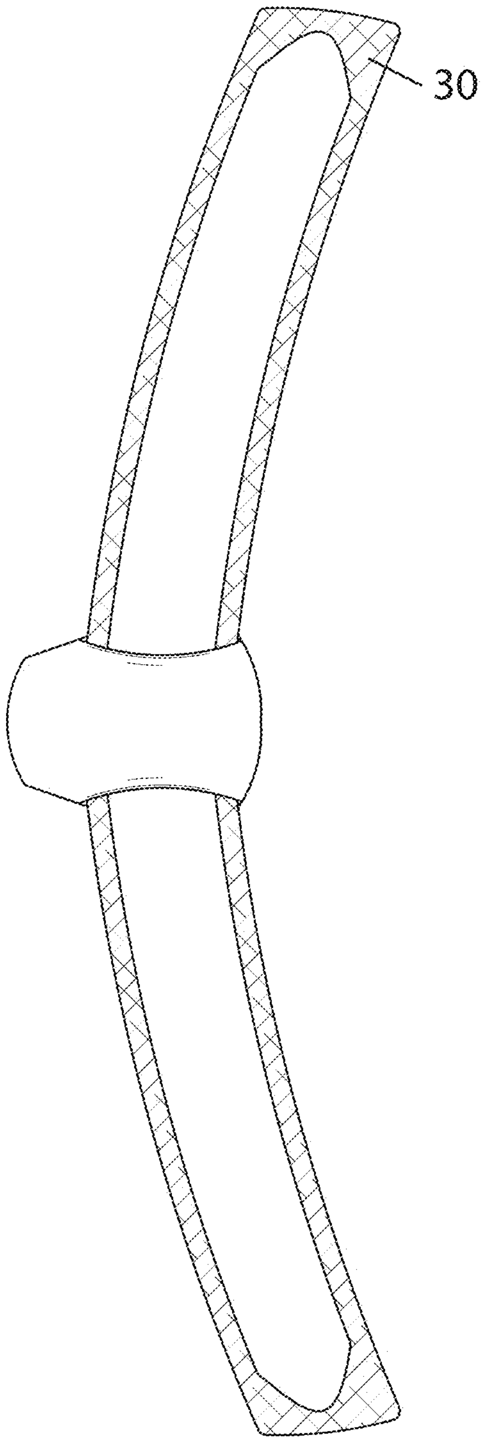
FIG. 3 is a perspective view of an exemplary embodiment of the present invention, shown in an uncinched condition.
Figure 4:
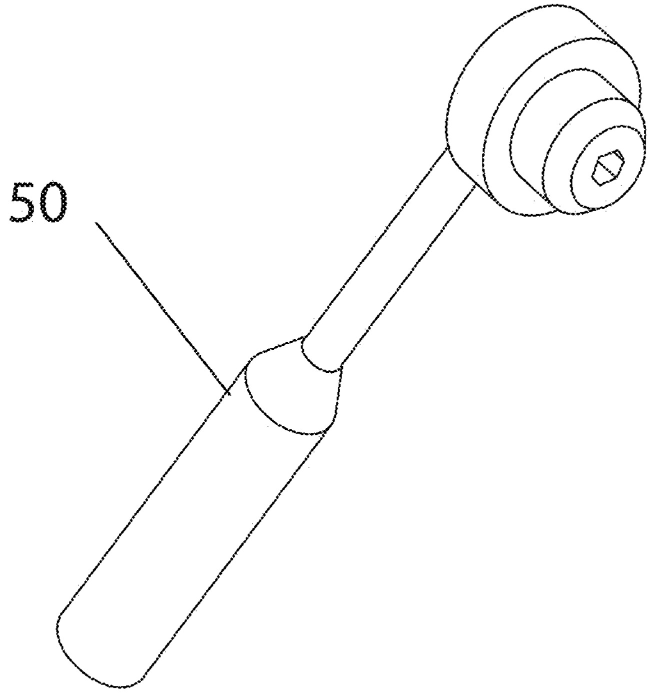
FIG. 4 is a perspective view of an ergonomic ratchet tightening tool of an exemplary embodiment of the present invention.
Figure 5:
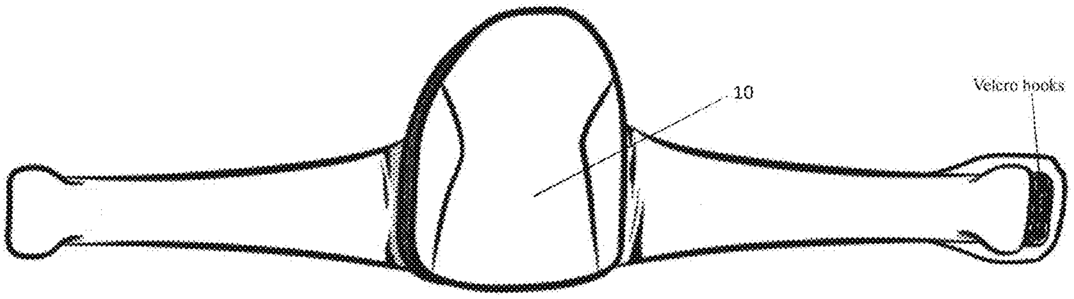
FIG. 5 is a front perspective view of an exemplary embodiment of the present invention.
Figure 6:
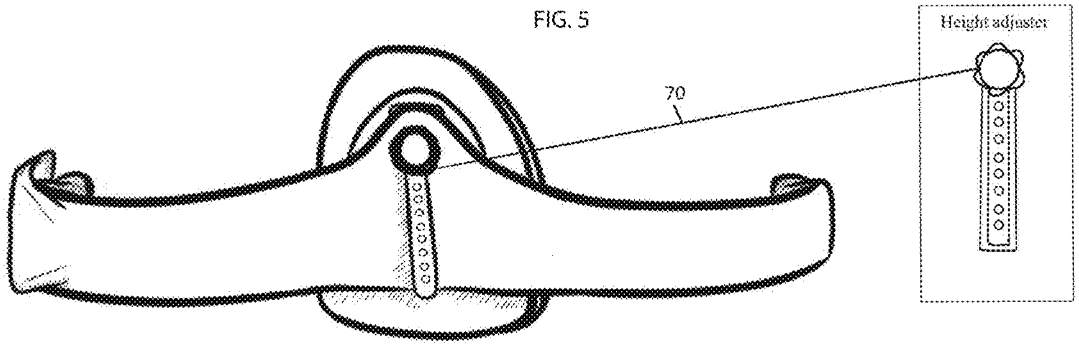
FIG. 6 is a rear perspective view of an exemplary embodiment of the present invention.
Figure 7:
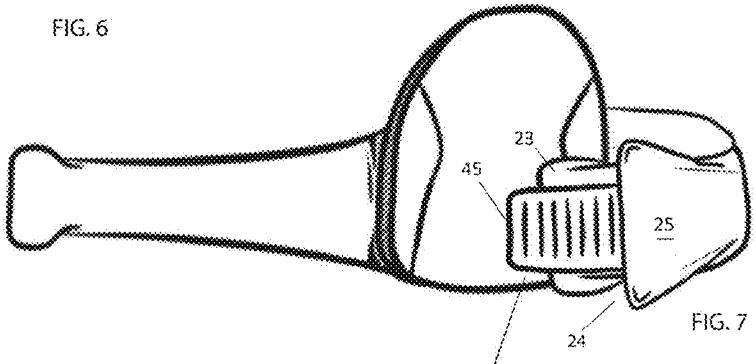
FIG. 7 is a front perspective view of an exemplary embodiment of the present invention, illustrating a distal end of the strap 20 detailing the male end 45 of the cinching band 41 protruding from two layers (an inner layer 23 and an outer layer 25) of the flap 20 that define a channel through which the cinching band 41 resides.
Figure 8:
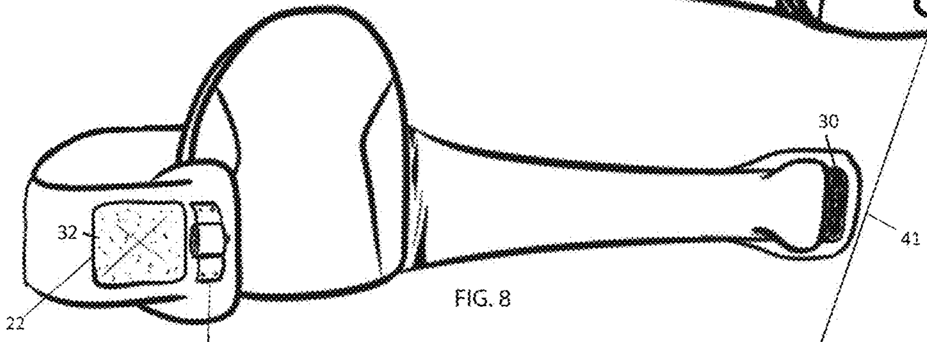
FIG. 8 is a front perspective view of an exemplary embodiment of the present invention, the first and second complementary fasteners 30 and 32 on the first and second distal ends of the flap 20, whereby the first and second complementary fasteners 30 and 32 can form an initial engagement between the distal ends of the flap 20. The initial engagement provides very little compressive force to the flap 20; rather, such an engagement mainly prevents the brace from falling off while the user utilizes the cinching mechanism to then apply sufficient circumferential compression of the flap 20 by way of the intrinsic cinching band 41.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Referring now to FIGS. 1 through 11, the present invention may include a lumbar spine brace 100 with mechanical cinching device for a patient to tighten and engage the 100 brace themselves. The lumbar spine brace 100 provides posterior back or lordotic arch support 10 operatively associated with a heavy-duty primary compression flap 20 extending from each of the two opposing peripheral edges of the posterior back support 10.

It is understood that the compression flap 20 may be the result of two flaps 20, one flap 20 extending from each longitudinal edge of the posterior back support 10. Alternatively, there may be one primary flap 20 that slides through a passage slot 12, channel, or the like provided by the posterior back or lordotic arch support 10. In any event, the primary flap(s) 20 may be composed of any material sufficient to enable the disclosure herein. Removable fasteners 30, 32 (including but not limited to hook and loop fasteners) may be provided along an engagement surface 22 adjacent each distal end of the primary flap 20.

The primary flap 20 may have an outer layer 25 and inner layer 23 that define a longitudinal channel which may be occupied by a cinch clamp band 41. An opening 24 in one of the distal ends of the primary flap 20 allows a loose end 45 of a cinch clamp band 41 to protrude therefrom. The cinch clamp band 41 is part of the mechanical cinching device an may be a strap of semirigid plasticized, metallic, or fiberglass, wherein the cinch clamp band 41 may be urged into a 'loop', with a mechanism to forcibly adjust the 'diameter' of that 'loop', thereby exerting a squeezing or circumferential compression force on an object circumscribed by or otherwise operatively associated with the cinch clamp band 41.

Figure 9A:
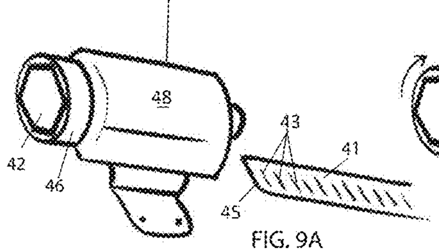
FIG. 9A is a perspective view of a cinching mechanism of an exemplary embodiment of the present invention, which comprising the cinching band 41 and the cinching screw 42 with a tool interface.
Figure 9B:
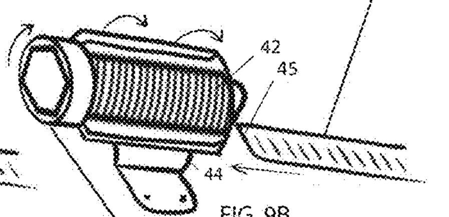
FIG. 9B is a perspective section view of an exemplary embodiment of the housing 48 of the cinching screw 42 of the present invention.
Figure 10A:
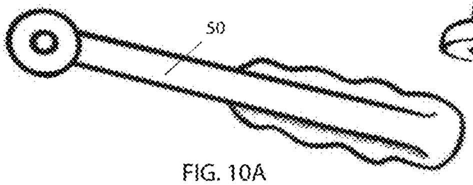
FIG. 10A is a perspective view of the ergonomic ratchet tightening tool of an exemplary embodiment of the present invention.
Figure 10B:
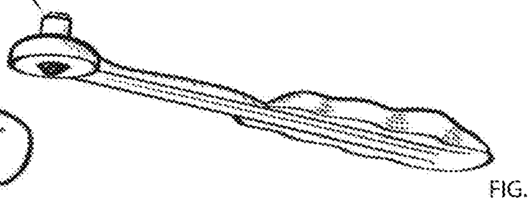
FIG. 10B is a perspective view of the ergonomic ratchet tightening tool of an exemplary embodiment of the present invention, illustrating its engagement with the tool interface 46 of FIG. 9B.

In one embodiment, the cinch clamp band 41 may be a flexible strap having a plurality of engagement points 43, which may be a screw thread pattern cut or pressed therein. One end of the cinch clamp band 41 is associated with a captive screw 42, while the oppose end is the loose end 45 that protrudes from the opening 24 so that the loose end 45 which can be fed into a narrow space between the band, clip, or plate and the captive screw 42, as illustrated in FIGS. 9A and 9B. When the screw 42 is turned, it acts as a worm drive pulling the threads of the band, causing the cinch clamp band 41 and thus the primary flap(s) 20 that envelope the cinch clamp band 41 to tighten around the patient (or when screwed the opposite direction, to loosen). The captive screw 42 may be other elements that can operatively associate with the cinching band 41 to tighten and so lessen that loop the cinching band 41 forms as it passes between the two distal ends of the flap 20.

A tool interface 46 (e.g., a hex bolt) may be provided on an exterior surface of the captured screw 42 that may enable tightening (e.g., through turning clockwise) and so facilitate the loose/male end of the cinching band 41 to tighten and lock in position with, in some embodiments, a pinion within a housing 48. The tightening moves the opposing flaps 20 from a disengaged condition (FIG. 3) to an engaged condition (FIGS. 1 and 2) for engaging a patient. The tool interface 46 on the captive screw 42 may be dimensioned and adapted to be operatively associated with a ratcheting device 50 that is ergonomic and easy to manipulate.

The primary flap 20 is the main foundation of the lumbar spine brace 100 which allows the posterior lumbar support piece 10 to attach and maintain position centrally on the lower back of the patient. The primary flap ends which are on the anterior surface of the patient, the belly, will have first fasteners 30 on the inside facing of the primary flap end and second fasteners 32 on the outside facing of the other primary flap end. The ends of the primary flaps 20 may open like a sleeve allowing the ends of the cinching band 41 to be exposed and allow interaction between the two ends of the flap 20. The distal end of the primary flap opposite the exposed male end of the cinching band 41 may contain the exposed interface 46 of the cinching mechanism 42 (which may be protected by a housing 48). The tool interface 46 provides a receptacle for the systemic tool 50 or 60. The tool interface 46 may be attached but exposed to the external environment through the heavy-duty primary flap 20 to be accessible to a ratcheting tightening and loosening tool 50 or 60.

Once the brace is donned in the appropriate position the loose male end protruding from one end of the primary flap 20 will slide into the mechanical cinching housing 48 (attached to the other end of the primary flap 20 by the way of a clip or the like 44) to operatively associated with the captive screw 42 in said housing 48. The opposing primary flap ends provide hook and loop fasteners 30 and 32 which may be overlain to establish an initial secured condition between the two ends of the primary flap 20. The initial secured condition is something that someone suffering from senile asthenia, arthritis or another manual disadvantage can achieve—i.e., it merely forms a locked engagement between the two ends of the primary flap 20, which may apply minimal compressive force to the wearer. The receptacle apparatus hex bolt facing anteriorly (away from the body) will be accessible to an ergonomic easy to use hex driver, which may be electrically powered, to tighten to the desired amount of compression.

The primary flap(s) 20 are made of heavy-duty nylon. The posterior back support 10 will be made of a heavy-duty nylon outer covering and a durable dense foam with fiberglass plate within the foam to maintain adequate durability. The posterior back support 10 may provide an adjustment device 70 that urges the posterior back support 10 relative to the primary flap 20 by way of a dial or other adjustment mechanism. This vertical adjustable track enables the posterior lumbar support pad 10 to be moved more cephalad (toward the head) or caudal (toward the feet) adding to its universality/versatility for "one size fits all". The adjustment device 70 may alter the relative elevation of the posterior back support 10 on the wearer after the primary flap is set in at least the initial secured condition (by way of only the removable fasteners 30 and 32).

The receptacle housing 48 will be made of metal with multiple metal spring loaded pinions inside of the apparatus which will receive the male end 45 of the cinching band 41 so that when they address the male end which is slotted the pinions will spring into the slots maintaining the position. The fiberglass/metal hex bolt exposed anteriorly will allow for the hex ratcheting tool to be easily accessible. The hex ratcheting tool will be made of a tubular metal. It may have a hex driver on one end and three right angles with a circular disc shape spinning handle (made of fiberglass) at the other end. Adjacent to the disc end will be a spindle shaped handle (made of fiberglass) that spins around the tubular metal construct.

Figure 11:
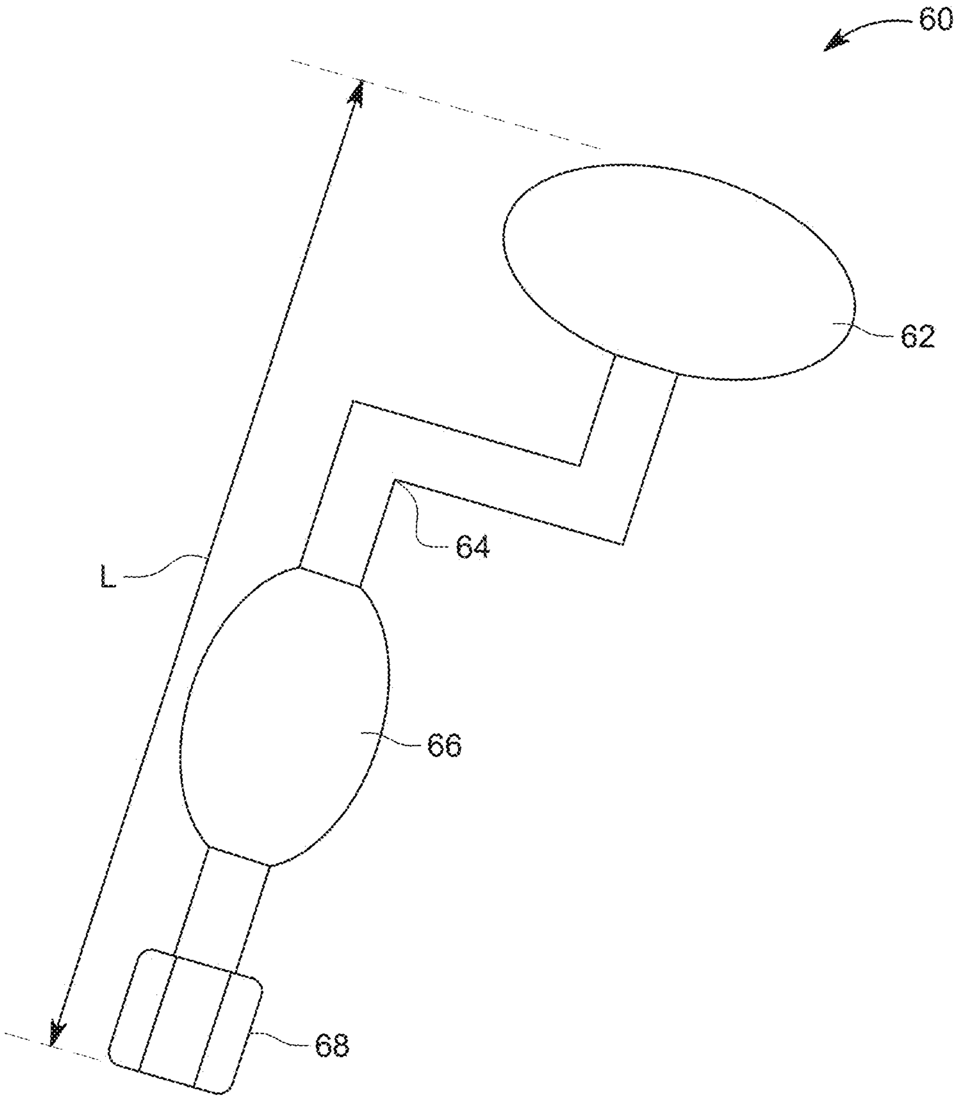
FIG. 11 is a schematic view of a mechanical cinching tool of an exemplary embodiment of the present invention.

Referring to FIG. 11, the systemic tool 60 may provide an ergonomic working handle 62, an articulating ratcheting joint 64, an ergonomic stabilizing handle 66, and a magnetic hex driver 68. The systemic tool 60 may have a hex nut adapter on the operative end 68 and the handheld pieces to spin on the axis. This allows the patient to push with a posteriorly vectored force into the abdomen to engage the hex nut on the brace (likely magnetic so that the tool does not disengage as easily) and rotate the ratcheting blue cylindrical disc handle (working handle) while stabilizing with the spindle handle 62 on the body of the tool to either tighten or loosen the hex nut. The tool will be light weight yet durable All are necessary elements for this brace to function most efficiently and effectively for patients with upper extremity deficits requiring lumbar spine support.

The present invention and the novelty of the apparatus may be used in other bracing systems; essentially the ability to wear a brace and tighten it without requiring significant upper body strength or dexterity can be utilized in osteoarthritis braces for the knee ("unloader braces") or the hip. Most people requiring braces aside from athletes have difficulty while applying braces and that is generally the reason that they are not compliant with wearing the braces/DME (durable medical equipment). Also, the present invention can create any DME (durable medical equipment) that requires upper body strength or dexterity to don or doff.

The compression flap 20 may be a harness-like strap that provides, by way of manipulating the cinching mechanism, circumferential compression about objects the flap/strap is wrapped around. As mentioned above, the flap/strap may define a diameter that may be selectively lessened or tightened by way of the cinching mechanism.

As used in this application, the term "about" or "approximately" refers to a range of values within plus or minus 10% of the specified number. And the term "substantially" refers to up to 80% or more of an entirety. Recitation of ranges of values herein are not intended to be limiting, referring instead individually to any and all values falling within the range, unless otherwise indicated, and each separate value within such a range is incorporated into the specification as if it were individually recited herein.

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object. Further, for purposes of this disclosure, the term "mechanical communication" generally refers to components being in direct physical contact with each other or being in indirect physical contact with each other where movement of one component affect the position of the other.

The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "up," "down," and the like, are words of convenience and are not to be construed as limiting terms unless specifically stated to the contrary.

It should be understood, of course, that the foregoing relates to exemplary embodiments of the invention and that modifications may be made without departing from the spirit and scope of the invention as set forth in the following claims.

What is claimed is:

1. A lumbar spine brace comprising:

a flap;

a posterior support connected to an approximate posterior midpoint of the flap, wherein the flap extends between a first end and a second end;

the flap provides a longitudinal channel through which a cinching band resides so that a male end of the cinching band protrudes from an opening along the first end; and a captured screw connected adjacent to the second end of the flap, wherein the captured screw provides a tool interface communicating with an external environment, wherein the cinching band is dimensioned and shaped to operatively associate with the captured screw rotatable via the tool interface whereby a circumferential compressive force is imparted on the flap.

2. The lumbar spine brace of claim 1, wherein the captured screw is disposed in a housing that is clipped directly to the second end of the flap.

3. The lumbar spine brace of claim 2, wherein the captured screw is directly connected to a female end of the cinching band.

4. The lumbar spine brace of claim 3, wherein the first and second ends of the flap provide hook and loop fasteners, respectively for establishing an initial secured condition, from which the cinching band reduces a diameter of the flap formed by way of the initial secured condition.

5. The lumbar spine brace of claim 4, wherein the cinching band provides a screw thread pattern for operatively associating with the captured screw.

6. The lumbar spine brace of claim 5, wherein the tool interface comprises a hex bolt interface.

7. The lumbar spine brace of claim 6, further comprising a systemic tool having a hex driver dimensioned and shaped to operatively associate with the hex bolt interface.

8. The lumbar spine brace of claim 7, wherein the hex driver is electrically powered.

9. The lumbar spine brace of claim 7, wherein the systemic tool provides a working handle directly connected to an articulating ratcheting joint, which in turn is directly connected to a stabilizing handle directly connected to the hex driver, and wherein the hex driver is magnetized.

10. The lumbar spine brace of claim 7, further comprising an adjustment device that urges the posterior support to move, relative to the flap, in the cephalad-caudad direction by way of a dial or track.

* * * * *